United States Patent [19]

Winder

[11] Patent Number: 5,472,690
[45] Date of Patent: Dec. 5, 1995

[54] MYCOHERBICIDE AND METHOD FOR CONTROLLING *CALAMAGROSTIS CANADENSIS*

[75] Inventor: Richard S. Winder, Sooke, Canada

[73] Assignee: Forestry Canada, Ottawa, Canada

[21] Appl. No.: 102,200

[22] Filed: Aug. 5, 1993

[51] Int. Cl.⁶ .............................. C12N 1/14; C12N 1/18; A01N 63/00
[52] U.S. Cl. .................. 424/93.5; 435/254.1; 435/256.5; 435/911; 435/929
[58] Field of Search .............................. 424/93 Q, 93.5; 435/254.1, 256.5, 911, 929

[56] References Cited

U.S. PATENT DOCUMENTS

| | | | |
|---|---|---|---|
| 3,849,104 | 11/1974 | Daniel et al. | 71/65 |
| 4,263,036 | 4/1981 | Charudattan | 71/66 |
| 4,419,120 | 12/1983 | Walker | 71/79 |
| 4,643,756 | 2/1987 | Cardina et al. | 71/79 |
| 4,715,881 | 12/1987 | Anderson et al. | 435/254.1 |
| 4,808,207 | 2/1989 | Gotlieb et al. | 71/73 |
| 4,940,834 | 7/1990 | Hurley et al. | 800/200 |
| 5,028,253 | 7/1991 | Watson et al. | 71/79 |
| 5,034,328 | 7/1991 | Boyette | 435/254.1 |
| 5,244,659 | 9/1993 | Watson et al. | 435/254.1 |
| 5,292,659 | 3/1994 | Cartwright et al. | 435/254.1 |

OTHER PUBLICATIONS

Winder, R. S., et al., "Phytopathology." vol. 82, #10, Oct. 1992, abstract #A860 on p. 1155.
ATCC Catalogue of Filamentous Fungi, 18th ed., 1991, pp. 181, 196. ed. S. C. Jong, et al.
Winder, Richard S. "The potential for biological control of bluejoint (*Calamagrostis Canadensis* [Michx.] Beauv.) in reforestation areas in British Columbia" *Biocontrol of Forest Weeds* Proc. of Workshop held at Western International Forest Disease Work Conference, Vernon, British Columbia, Aug. 9, 1991, Charles Dorworth and S. G. Glover, eds.; Forestry Canada; pp. 30–36; 1992.
Carroll, G. O., "Trans. Mycol. Soc. Japan" vol. 31, #1, pp. 103–116, 1990.
White, J. F. et al, "Mycologia" vol. 77, #3, pp. 487–489, 1985.
Mäkelä, K., "Annalis Agriculturae Ferriae," vol. 30, 133–155, 1981.
Chiang, M. Y. et al., "Weed Science" vol. 37, pp. 802–809, 1989.

*Primary Examiner*—Marian C. Knode
*Assistant Examiner*—Kristin Larson
*Attorney, Agent, or Firm*—Bell, Walter & Brousseau

[57] ABSTRACT

The mycoherbicide of the present invention is effective in the control of *Calamagrostis canadensis* and/or related grasses, particularly in areas undergoing reforestation. The mycoherbicide includes one or both of *Fusarium nivalis* (ATCC #26050) and a fungus, *Colletotrichum calamagrostidis* (PFC-215, ATCC #74287), isolated from a diseased plant of *C. canadensis* var. *canadensis*. The mycoherbicidal formulation preferably includes an allelopathic agent, such as straw, straw-based material, straw extract, grass extract or an endophyte. An especially effective treatment was demonstrated with *C. calamagrostidis* (PFC-215) and an inoculum of endophytic *Fusarium nivalis*. An embodiment of a method of treatment according to the present invention includes the application of endophytes of reduced virulence to grass bordering a target area or in grazing lands, to prevent either natural or inoculative infection.

24 Claims, 1 Drawing Sheet

MYCOHERBICIDE AND METHOD FOR CONTROLLING *CALAMAGROSTIS CANADENSIS*

FIELD OF THE INVENTION

The present invention relates to a composition and a method for biological control of undesirable vegetation and, in particular, to a mycoherbicide and a method for controlling weeds, such as *Calamagrostis canadensis* and related grasses, particularly in areas undergoing reforestation.

BACKGROUND OF THE INVENTION

There is presently considerable demand for the reforestation of logging sites. However, young tree seedlings, such as spruce, do not always grow successfully once planted on such sites. A primary cause of failed spruce regeneration in Canada and the United States is the weed *Calamagrostis canadensis* (Michaux) Beauv., also known as bluejoint, reed grass and marsh reed grass.

Bluejoint is a grass species of the taxonomic family Graminaceae consisting of a complex of at least eight subspecies. *C. canadensis* is a perennial rhizomatous grass found in pine, spruce, and mixed-wood forests, open uplands and marshy sites throughout North America north of 35° latitude (Lieffers et al "Ecology of and control strategies for *Calamagrostis canadensis* in boreal forest sites" *Can. J. Forestry Research* 23:2070–2077 (1993). The grass is very hardy, thriving in a wide variety of habitats including arctic environments, and in a wide range of moisture and nutrient regimes.

Bluejoint infestation is a serious problem in the disturbed open sites of reforestation areas where the weed can form continuous mats within about 3 to 4 years. At this stage the aboveground biomass may be up to 687 g/m$^3$ (Lieffers et al, *Can J For Res*). Bluejoint grows profusely to a height of about 2 m or more, overwhelming young tree seedlings. In particular, bluejoint competes very strongly with the seedlings for nutrients, water and light. Furthermore, dense litter from the weed can cause snow-press and smothering problems, and can delay spring soil thaw. The litter also halts natural regeneration by preventing seeds from reaching the ground before desiccation. Bluejoint can cause seedlings to pitch-over and grow laterally. Moreover, weed litter can also provide a safe haven for seedling-eating mammals such as rabbits.

As a consequence of the above factors, *C. canadensis* can delay spruce development for up to 10 years, thereby seriously impairing reforestation efforts and timber production. A method of controlling the weed, especially in reforestation sites, is imperative.

There is currently much concern about the use of synthetic chemical herbicides, such as glyphosate, to control weeds. Consequently, the use of synthetic chemical herbicides is already barred or restricted in many areas of Canada and the United States.

Other non-chemical approaches to weed control have been considered including grazing by sheep, burning, mowing, mounding, trenching and mulching. These options are not generally viable and are impractical for reforestation sites. For example, burning is effective only with deep slash burning as the perennial rhizomes of the weeds regenerate readily. In fact, fire can have a rejuvenating effect on *C. canadensis* leading to large increases in biomass and seed production (Lieffers et al, *Can J For Res* 23:2070–77).

However, deep burning has a devastating environmental impact. Mounding and trenching are also very destructive techniques. Sheep grazing techniques are expensive. While mulching is suitable for small private gardens, it is impractical and too labour intensive for large reforestation sites. Furthermore, complete weed eradication may be counterproductive, leading to wide-ranging problems including soil erosion, excessively high soil temperatures, and other negative phenomena.

The use of bioherbicides as biocontrol agents is therefore attracting considerable attention. Bioherbicides are typically endemic and applied inundatively to control undesired vegetation. In particular, mycoherbicides are bioherbicides which are fungal plant pathogens. The principal objective in dealing with weeds is to reduce competition from the weeds so as to allow the desired plants to grow freely. Accordingly, biocontrol of weeds addresses concerns about the effects of chemicals on environmental integrity and human health.

A variety of mycoherbicides have been proposed to control specific weeds. For example, Canadian Patent Number 1,224,055 (Watson et al, Jul. 14, 1987) describes the use of *Colletotrichum coccodes* for controlling velvetleaf and U.S. Pat. No. 4,643,756 (Cardina et al, Feb. 17, 1987) describes the use of *C. truncatum* for controlling Florida beggarweed. U.S. Pat. No. 4,776,873 (Caulder et al, Oct. 11, 1988) teaches a synergistic herbicidal composition comprising *Alternaria cassiae* and chemical herbicides for controlling sicklepod.

Inundative methods can achieve results ranging from partial to complete weed control or mortality, depending on the nature of the particular pathosystem, the formulation, and the virulence and concentration of inoculum. In particular, in order to control bluejoint, the bioherbicide should deplete carbohydrate reserves in the rhizomes in order to prevent rapid regeneration.

An effective bioherbicide causes disease in the target weed without adversely affecting the growth of crop plants. Factors which must be considered are that crop plants may be more susceptible to disease than a typical weed with its "wild type" resistance to pathogens. In addition, only certain parts or stages of the plant may be susceptible to the disease and major fluctuations in temperature, humidity, precipitation, or dew period can inhibit disease development. In terms of the pathogen, virulence may be difficult to maintain during inoculum production and storage.

It is an object of the present invention to provide an environmentally acceptable alternative to synthetic chemical herbicides for the control of weeds, such as *Calamagrostis canadensis* and related grasses.

It is another object of the present invention to provide a mycoherbicide for controlling *C. canadensis* and related grasses in coniferous reforestation areas.

SUMMARY OF THE INVENTION

According to one aspect of the present invention, there is provided a mycoherbicide for controlling *Calamagrostis canadensis* and/or related grasses, comprising an inoculum of a fungus selected from *Colletotrichum calamagrostidis* (PFC-215, ATCC #74287), *Fusarium nivalis* (ATCC #26050) and isolates, descendants and mutants thereof, in an amount sufficient to control growth of *C. canadensis* and/or related grasses.

According to another aspect of the present invention, there is provided a method for controlling or preventing growth of *Calamagrostis canadensis* and/or related grasses, comprising the step of inoculating a target area of *C. canadensis* and/or related grasses with an effective amount of a mycoherbicide comprising an inoculum of a fungus selected from *Colletotrichum calamagrostidis* (PFC-215, ATCC #74287), *Fusarium nivalis* (ATCC #26050) and isolates, descendants or mutants thereof.

According to a further aspect of the present invention, there is provided the fungal species *Colletotrichum calamagrostidis* (PFC-215), ATCC #74287 and isolates, descendants and mutants thereof.

BRIEF DESCRIPTION OF THE DRAWINGS

In the accompanying drawing which illustrates embodiments of the present invention.

DETAILED DESCRIPTION OF THE PREFERRED EMBODIMENTS

Figure 1:
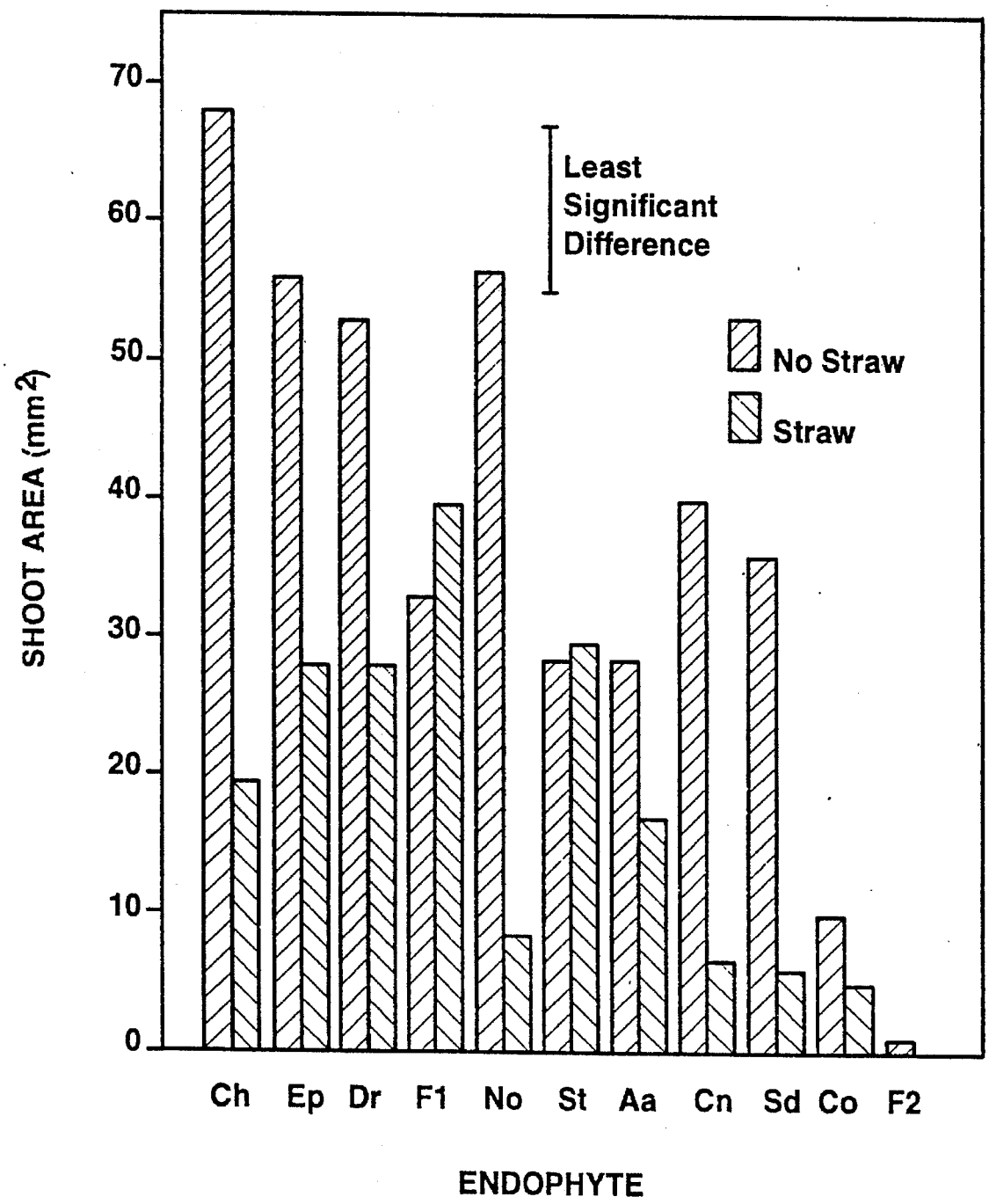
FIG. 1 is a graphical representation of the synergistic effect on *Calamagrostis canadensis* of endophytes and straw with a mycoherbicide in accordance with the present invention.

*Calamagrostis canadensis* and related grasses, such as *C. rubescens* (pinegrass), *C. stricta* and *C. purpurascens* are suppressed by a highly integrated inundative biocontrol approach without adversely affecting most other plants, including conifers. This biocontrol approach is particularly useful in reforestation areas.

The mycoherbicide of the present invention is formulated with one or more fungi isolated from diseased *C. calamagrostis* and/or related grasses. One such fungi is *Colletotrichum calamagrostidis* (#PFC-215, ATCC #74287).

The novel endemic fungal species *Colletotrichum calamagrostidis* (isolate #PFC-215, ATCC #74287) was isolated from diseased *C. canadensis* var. *canadensis* in northern British Columbia, Canada. *C. calamagrostidis* (PFC-215, ATCC #74287) causes disease in *C. canadensis*. The microorganism was deposited at the Pacific Forestry Center, Forestry Canada on Dec. 30, 1992, and given isolate #PFC-215. The microorganism was also deposited with the American Type Culture Collection, 12301 Parklawn Drive, Rockville, Md. on Jun. 22, 1994, and assigned ATCC #74287.

Diseased leaves of *C. canadensis* were collected near Groundbirch, British Columbia, Canada in June, 1991. Excised lesions were surface sterilized by immersion in 70% ethanol for 30 seconds, followed by immersion in 10% HClO for 4 minutes. The excised lesions were rinsed in sterile water, placed in Petri plates containing Potato Dextrose Agar (PDA), and incubated 20 cm under fluorescent lights (12 hour diurnal period) for 3 days. Colonies of *C. calamagrostidis* (PFC-215) were transferred to fresh PDA plates and subsequently transferred to PDA slants for storage at 5° C. Inoculum was generated by transfer from slant cultures to Petri dishes containing PDA. These cultures were incubated under fluorescent light, as described above, for 7 days. Spores were harvested from the cultures with a sterile scalpel and transferred to 500 ml flasks containing potato dextrose broth, for example a 10% dextrose broth. The liquid cultures were incubated for 7 days on a shaker platform (100 rpm).

Taxonomic characteristics of *C. calamagrostidis* (PFC-215, ATCC #74287) are as follows:

Colonies on potato dextrose agar are grey, reverse light orange and grey, with a regular margin. In low light, colonies produce non-sporulating, dense, felty, dark grey aerial mycelia, with raised patches of light grey covering dense, dark, globular patches of hyphae and sclerotia instead of acervuli. Globular patches, when imbedded in the medium, may be accompanied by a large number of appressoria.

Sclerotia develop as thickened acervuli, spherical or oblong, along leaf veins, immersed to superficial, dark red-brown to black, occasionally with rudimentary setae but mostly surrounded by thick, branched, segmented hyphae, abundant in low light or cold temperatures. Sclerotia are 12–192 µm×12–96 µm.

Acervuli on leaf and stem lesions are setose, mostly elongated and 24–240 µm×24–84 µm. Setae are 24–144 µm long, approximately 4–7 µm wide at the base, with the base thicker than the apex. Setae are brown, with rounded apex, rarely septate and abundant.

Conidia are salmon-orange en masse, hyaline, aseptate, slightly falcate, fusiform, with obtuse apices, 15–28 µm×2–5 µm, with an average of 22.5 µm×3.9 µm. Conidia associated with globular patches may be non-falcate and highly guttulate. Conidiophores are aseptate, hyaline, cylindrical, phialidic and approximately 12–20 µm×2–5 µm.

Appressoria are abundant, dark olive-brown, clavate, with regular edges, and occasionally very slightly 1-lobed. The average size of appressoria is 12.2 µm×8.0 µm (7–21 µm×5–12 µm). Hyphal cells producing the appressorium are occasionally lightly pigmented.

The fungus has two modes of existence. It can attack the living tissue of its specific host or survive as a saprobe on plant litter, agar media, senescent leaves, and the like. *C. calamagrostidis* (PFC-215) is host-specific and only mildly infests senescent leaves of certain grasses. This is more clearly demonstrated in Example 3.

The method involves inoculating *C. canadensis* with *C. calamagrostidis* (PFC-215), as a mycoherbicide. The mycoherbicide may be combined with a carrier, such as clay and/or alginate, and formed into pellets. Hyphae and/or conidia from the cultures of *C. calamagrostidis* (PFC-215) can be incorporated into pellets by techniques known to those skilled in the art. For example, hyphae can be incorporated into alginate pellets using the method of Boyette and Walker (*Phytopathology* 75:183–185; 1985). Another method of preparing mycoherbicide pellets is disclosed in U.S. Pat. No. 4,718,935 (Walker et al, Jan. 12, 1988).

The pellets can be broadcast over the desired area. Alternatively, the pellets can be ground into a coarse dust and combined with a non-phytotoxic surfactant, such as 2% Soy-Dex®, a soy oil and surfactant mixture (Helena Chemical Co., Memphis, Tenn.). The pellets are then sprayed, dusted or broadcast onto an area where *C. canadensis* and/or related grasses are growing, in an amount sufficient to control the weed. Alternatively, the pellets may be ground prior to application or the mycoherbicide may be prepared in a liquid form. The mycoherbicide may have incorporated therein or associated therewith, chemical herbicides, nutrients, metabolites and/or antibiotics.

The mycoherbicide can be applied to the desired area before the grass emerges in the spring or, shortly thereafter, to emerging grass seedlings or tillers. Preferably, the mycoherbicide is applied to seedlings or tillers of *C. canadensis* and related grasses in the 1–3 leaf stage. The application rate should be in the range of from about 1 to about $10^9$ cfu (colony forming units)/m² of target area. Preferably, the application rate should be in the range of from about $10^5$ to about $10^9$ cfu/m². Application rates less than $10^5$ cfu/m² are primarily useful in a formulation with a synergistic herbicide.

The attack of the mycoherbicide on these grasses is manifested by the appearance of brown lesions or necrotic areas, followed by wilting and death of the plant. In field testing with the dust, the mycoherbicide achieved about 50% biomass reduction under certain conditions, without damage to conifers or other non-target flora.

In a preferred embodiment, an allelopathic agent, such as straw, straw-based material, straw extract, grass extract or an endophyte, is incorporated in or associated with the mycoherbicidal formulation as a factor to predispose C. canadensis to attack by the mycoherbicide. The allelopathic agents may be derived from C. canadensis or other plants. Example 4 demonstrates the synergistic effect of the mycoherbicide of the present invention and self-allelopathic stress due to straw accumulation, whether naturally present or simulated by the addition of one or more of the above-mentioned allelopathic agents. Naturally occurring endophytes which can be triggered into pathogenic (disease-causing) modes by straw extracts include Epicoccum sp., Fusarium sp., *Fusarium nivalis* (ATCC #26050), Chaetomium sp., *Alternaria alternata*, Stemphyllium sp., Drechslera sp. and *Colletotrichum calamagrostidis* (PFC-215, ATCC #74287) itself.

The above-mentioned endophytes were tested and the results are discussed in Example 4. Some of the endophytes blocked damage from *C. calamagrostidis* (PFC- 215), despite creating their own disease. The application of the mycoherbicide of the present invention may involve the application of one of these particular endophytes to block damage where the action of mycoherbicide is not desired, for example, on grass bordering the target area or in grazing lands, to prevent inoculative or natural infection.

The following Examples illustrate the invention.

EXAMPLE 1

Hyphae from four 10% dextrose liquid cultures and conidia from four potato dextrose agar cultures of *C. calamagrostidis* (PFC-215) were incorporated into a 2% (w/v) sodium alginate, 20% (w/v) kaolin clay, and 150 mg streptomycin sulfate/ml solution, solidified in 0.25M $CaCl_2$, dried and ground to a powder. The conidia were pretreated with a tannic acid solution to remove the inhibitory matrix. The pre-treatment method is disclosed in U.S. Pat. No. 5,244,659.

The mycoherbicide formulations were tested in a greenhouse for the ability to attack *C. canadensis* plants. The plants were watered until runoff and dusted with 0.01 g/m² powder.

Plants dusted with conidial powder exhibited no significant damage. Hyphal dust caused 36±1% leaf area damage (LAD) after 46 hours of dew. The efficacy of the mycoherbicide increased to 53±3% LAD when 2% Soy-Dex® surfactant was employed as a wetting agent.

A solution of 132 g/L hyphae in 0.5% alginate was also tested for its effectiveness as a mycoherbicide. With 16 hours of dew, plants were sprayed with the solution until runoff. After 1 week, the mycoherbicide had caused 30% biomass reduction and 30% LAD.

EXAMPLE 2

The effect of straw residue and the mycoherbicide was tested in a boreal forest on a 1 ha site near the original collection point of *C. calamagrostidis* (PFC-215), where infestation by *C. canadensis* ranged from nil to profuse and declining towards the willow stage. Six 2 m×2 m plots were staked out at random locations within the site, just as tillers were emerging. A generalized randomized complete block design was used, with 3 blocks assigned according to straw depths of 0, 15, and 30 cm above the soil surface. Three random plots were treated with a hyphal formulation of *C. calamagrostidis* (PFC-215), according to the method described in Example 1, broadcast at the rate of 2.5 kg/ha. The remaining plots were treated with the wetting agent alone (500 L/ha). Within each plot, a 1 m² sample area was chosen with a population density of approximately 50 tillers/m². Tillers from the area were cut at the soil line and the fresh weight and total area damaged or diseased for each plant was recorded.

Although there were light snow flurries and an air temperature of 4° C. during application, the mycoherbicide caused disease and biomass loss in straw depths of 30 cm. However, *C. canadensis* in inoculated plots with 0 to 15 cm of straw was stimulated (Table I). The difference did not appear to be due to a sheltering effect from the straw, since disease was concentrated in leaf tips which were located well above the straw and was present in plots without straw. Unlike shoots from control plots, shoots harvested from inoculated plots continued to decay rapidly in cold storage (5° C.), indicating that the fungus is cold-tolerant. No disease was evident on conifers or other non-target species in the plots. Although straw may have an insulating effect on soil temperature, leading to a reduction in the rate of growth, this does not account for the observed differences in plant weights between control and treated plants.

TABLE I

| Inoculum (kg/ha) | Straw Height (cm) | Mean Fresh Wt. (g/plant) | Mean LAD (%) |
|---|---|---|---|
| 0.0 | 0 | 0.163 | 5.5 |
|  | 15 | 0.147 | 5.5 |
|  | 30 | 0.120 | 3.6 |
| 2.5 | 0 | 0.253 | 15.4 |
|  | 15 | 0.243 | 13.5 |
|  | 30 | 0.070 | 11.9 |
| (LSD) Least Significant Difference |  | 0.010 | 5.3 |

EXAMPLE 3

*C. calamagrostidis* (PFC-215) was tested to determine the host range with a hyphal dust mycoherbicide, as described in Example 1. The plants were 4 weeks old and were treated with 2% Soy-Dex® surfactant prior to dusting.

The effect of the mycoherbicide is listed in Table II as a disease rating of hypersensitivity, opportunism, disease and no reaction. Hypersensitivity is a type of resistance reaction in a plant which results in very rapid, very light damage from which the host recovers. Disease reactions are slower and more fatal. Opportunism indicates the colonization of substantially defenceless senescent leaves. Other than diseased senescent leaves, the plant is substantially unaffected by the mycoherbicide.

TABLE II

| HOST | DISEASE REACTION |
|---|---|
| C. canadensis | Disease |
| Rye | Hypersensitive |
| Barley | Hypersensitive |

TABLE II-continued

| HOST | DISEASE REACTION |
|---|---|
| Wheat | Opportunism |
| Corn | No reaction |
| Oats | Opportunism |
| Annual ryegrass | No reaction |
| Perennial ryegrass | No reaction |
| Kentucky bluegrass | No reaction |
| Colarado maple bean | Hypersensitive |
| Green bean | No reaction |
| Niger | No reaction |
| Sunflower | Hypersensitive |
| Savoy cabbage | Hypersensitive |
| Rutabaga | No reaction |
| Poppy | No reaction |
| Pepper | No reaction |
| Cucumber | No reaction |
| Safflower | No reaction |
| Lettuce | No reaction |
| Rapeseed | No reaction |

EXAMPLE 4

The effect of *C. calamagrostidis* (PFC-215) in combination with straw extracts and/or endophytes on *C. canadensis* was tested in Petri plates.

Free-standing straw of *C. canadensis* was collected and stored at 5° C. until use. A straw extract was prepared by macerating 20 g of straw in 1L of distilled water in a blender for 30 seconds. The maceration solution was allowed to soak for 24 h at 5° C. before being clarified by vacuum filtration through filter paper.

Plant growth solutions were prepared using 1 mM $NH_4H_2PO_4$, 5.7 mM $Ca(NO_3)_2$, 1.3 mM $CaCl_2$, 2 mM $MgSO_4.7H_2O$, 6 mM $KNO_3$, 24 µM $H_3BO_3$, 0.24 µM $CuCl_2.2H_2O$, 4.6 µM $MnCl_2.4H_2O$, 0.9 µM $ZnCl_2$, 0.1 µM $H_2MoO_4.H_2O$, and 75.9 µM Fe EDTA in distilled water and in the straw extract. The Fe EDTA was prepared by dissolving 1340 mg disodiumethylenediaminetetraacetate $(Na_2C_{10}H_{14}O_8N_2.2H_2O)$ in 500 ml of distilled water, heating for 5 minutes on a hot plate, and adding 990 mg $FeSO_4.7H_2O$. The resulting Fe EDTA solution was added (2 ml/L) to the growth solution.

The growth solutions were autoclaved with 10 g agar/L for 10 minutes to produce standard growth agar (SGA, distilled water in growth solution) or straw extract agar (SEA, straw extract in growth solution). The Petri plates were provided with a central divider so that one half of each plate contained SGA and the other half contained SEA.

Seeds of *C. canadensis* were collected and removed from glumes manually and placed into empty teabags for surface sterilization by immersion in 70% ethanol for 30 s, followed by immersion in 10% HClO for 4 minutes and a subsequent sterile water rinse. Seeds were placed in each half of each plate. The plates were sealed and placed in a growth chamber (20° C., 12 h diurnal light period).

The following endophytes were isolated from diseased *C. canadensis*: Chaetomium sp., Epicoccum sp., Drechslera sp., Fusarium sp., Stemphyllium sp., *Alternaria alternata* and *Fusarium nivalis.* Cultures were transferred to PDA plates and stored using the same method used for *C. calamagrostidis* (PFC-215). Plugs from the cultures were transferred to the SGA/SEA plates after 7 days. After inoculation, the plates were resealed and replaced in the growth chamber under the same conditions as above. After 7 days, the seedlings were inoculated with conidia of *C. calamagrostidis* (PFC-215), using a paint brush to apply a solution of $10^6$ conidia/ml in 2% Soy-Dex® surfactant. The plates were resealed and replaced in the growth chamber after the second inoculation. After a few days, the plants were analyzed for seedling vigor as defined by the following equation:

$$SVI=(\textit{leaf area in } cm^2 - \%\ LAD) + (\textit{root length in cm} \times \textit{number})$$

wherein SVI denotes the Seedling Vigor Index, and leaf area is estimated by the leaf length times the maximum leaf width. The results are presented in Table III.

TABLE III

| Endophyte | Seedling Vigor Index SEA | SGA |
|---|---|---|
| *Alternaria alternata* | 16.8 | 28.3 |
| Chaetomium sp. | 19.2 | 67.1 |
| *C. calamagrostidis* (PFC-215) | 5.3 | 9.1 |
| Drechslera sp. | 26.5 | 53.1 |
| Epicoccum sp. | 26.7 | 55.6 |
| Fusarium sp. | 39.7 | 32.1 |
| *F. nivalis* (PFC-271) | 0.0 | 0.5 |
| Stemphyllium sp. | 28.7 | 28.0 |
| Controls | | |
| No endophyte | 8.3 | 53.1 |
| Surfactant only | 6.2 | 35.6 |
| No treatment | 5.7 | 39.0 |
| LSD | 14.1 | 14.1 |

Generally, seedlings growing in SEA were less healthy than those growing in SGA. Straw extract inhibited the degree of radicle penetration (DRP) into the agar medium. Seedlings growing in SGA were also spindly and chlorotic. Both endophytes and straw extract contributed to increased disease levels, but endophytes also stimulated plants by enhancing DRP where straw extract was present. Presumably, enhanced DRP resulted from degradation of toxins by the fungi. Endophytes greatly enhanced shoot vigor and root vigor, although the enhancement of root vigor was diminished where straw extract was present. These data indicate that straw extract stresses *C. canadensis,* which matches the earlier field observations.

*C. calamagrostidis* (PFC-215), alone and in interaction with straw extract and/or endophyte, produced significant effects on vigor. Overall, inoculation with the mycoherbicide produced results ranging from stimulation or nil effect to complete mortality, depending on the conditions present. In the controls, straw extract clearly inhibited seedling vigor. Application of *C. calamagrostidis* (PFC-215) in SGA increased vigor in the absence of endophytes, and in the presence of Chaetomium sp., Epicoccum sp. and Drechslera sp. Vigor was reduced in the presence of *F. nivalis* and endophytic *C. calamagrostidis* (PFC-215), due to disease occurring at a presumably susceptible stage. Vigor was relatively unchanged in the presence of Fusarium sp., Stemphyllium sp. and *Alternaria alternata.*

In SEA, vigor was enhanced in the presence of Chaetomium sp., *Alternaria alternata,* Stemphyllium sp., Drechslera sp., Epicoccum sp. and Fusarium sp. The fungus of the present invention, *C. calamagrostidis* (PFC-215), caused complete mortality in the presence of *F. nivalis,* and severe inhibition in the presence of endophytic *C. calamagrostidis* (PFC-215) and in the absence of endophytes. Again, reduction in vigor by *F. nivalis* and *C. calamagrostidis* (PFC-215) was due mostly to pathogenesis at an earlier stage. Comparing SGA with SEA, vigor in SEA was lower in the presence of Epicoccum sp., Chaetomium sp. and Drechslera sp., and in the absence of endophytes. Vigor was not significantly different in the presence of Stemphyllium sp., *Alternaria alternata*, Fusarium sp. and *F. nivalis*.

FIG. 1 illustrates the effect of *C. calamagrostidis* (PFC-215) with endophyte and/or straw extract on shoot area. The abbreviations used in FIG. 1 are as follows: Chaetomium sp. (Ch), Epicoccum sp. (Ep), Drechslera sp. (Dr), Fusarium sp. (F1), Stemphyllium sp. (St), *Alternaria alternata* (Aa), *Fusarium nivalis* (F2) and *C. calamagrostidis* (PFC-215) (Co); the sample with no endophyte is shown as No; Cn and Sd represent the results for the Control (containing no mycoherbicide and no endophyte) and the plant treated with Soy-Dex® surfactant alone (no mycoherbicide, no endophyte), respectively.

Epicoccum sp., Fusarium sp., Chaetomium sp., *Alternaria alternata*, Stemphyllium sp. and Drechslera sp. blocked damage from *C. calamagrostidis* (PFC-215) to various degrees, despite creating their own disease. It may be desirable to include the application of these particular endophytes to block damage where the action of mycoherbicide is not desired, for example, on grass bordering the target area or in grazing lands, to prevent either natural or inoculative infection.

When *C. calamagrostidis* (PFC-215) was also used to inoculate the seed prior to germination, damage was probably enhanced by the effects of growth stage, longer incubation period, etc.

Of all of the endophytes, inoculation of the seeds prior to germination with *F. nivalis* (PFC-271) produced the lowest viability with or without straw extract. Example 4 demonstrates that the mycoherbicide formulation of the present invention is effective in controlling *C. canadensis* when comprised of one or both of *C. calamagrostidis* (PFC-215) and *F. nivalis*.

I claim:

1. A mycoherbicide composition for suppressing *Calamagrostis canadensis* comprising an inoculum of a fungus selected from the group consisting of *Colletotrichum calamagrostidis* (PFC-215, ATCC #74287), *Fusarium nivalis* (ATCC #26050), mutants of *C. calamagrostidis* ATCC #74287 and mutants of *F. nivalis* ATCC #26050 which possess mycoherbicidal activity, in an amount sufficient to suppress growth of *C. canadensis*.

2. A mycoherbicide composition according to claim 1, wherein the inoculum is a hyphal or conidial inoculum.

3. A mycoherbicide composition according to claim 1, further comprising an allelopathic agent selected from the group consisting of straw, straw extracts, and grass extracts.

4. A mycoherbicide composition according to claim 1, further comprising a chemical herbicide.

5. A mycoherbicide composition according to claim 4, wherein the mycoherbicide is in the form of pellets, dust or a solution.

6. A mycoherbicide composition according to claim 1, further comprising a surfactant.

7. A mycoherbicide composition according to claim 1, further comprising clay or alginate.

8. A mycoherbicide composition according to claim 1, further comprising a nutrient.

9. A mycoherbicide composition according to claim 1, further comprising an antibiotic.

10. A mycoherbicide composition according to claim 1, wherein the fungus is *Colletotrichum calamagrostidis* ATCC #74287.

11. A method for suppressing or preventing growth of *Calamagrostis canadensis*, comprising the step of inoculating an area of *C. canadensis* with an effective amount of a mycoherbicide composition comprising an inoculum of a fungus selected from the group consisting of *Colletotrichum calamagrostidis* (PFC-215, ATCC #74287), *Fusarium nivalis* (ATCC #26050), mutants of *C. calamagrostidis* ATCC #74287 and mutants of *F. nivalis* ATCC #26050 possessing mycoherbicidal activity.

12. A method according to claim 11, wherein the inoculation is carried out at a pre-emergent stage of the grass, or a post-emergent stage of the grass, or both a pre-emergent and a post-emergent stage of the grass.

13. A method according to claim 11, wherein the inoculum is a hyphal or conidial inoculum.

14. A method according to claim 11, wherein the inoculum is applied to an area at a concentration in the range of from about 1 to about $10^9$ cfu/m$^2$.

15. A method according to claim 11, wherein the inoculum is applied to an area at a concentration in the range of from about $10^5$ to about $10^9$ cfu/m$^2$.

16. A method according to claim 11, wherein the mycoherbicide composition further comprises an allelopathic agent selected from the group consisting of straw, straw extracts, and grass extracts.

17. A method according to claim 11, wherein the mycoherbicide composition further comprises a chemical herbicide.

18. A method according to claim 17, wherein the mycoherbicide composition is in the form of pellets, dust or a solution.

19. A method according to claim 11, further comprising the step of pretreating the *C. canadensis* with a surfactant.

20. A method according to claim 11, further comprising the step of pretreating the *C. canadensis* with an allelopathic agent selected from the group consisting of straw, straw extracts, and grass extracts.

21. A method according to claim 11, wherein the mycoherbicide composition further comprises a surfactant.

22. A method according to claim 11, wherein the mycoherbicide composition further comprises clay or alginate.

23. A method according to claim 11, wherein the mycoherbicide composition further comprises a nutrient.

24. A method according to claim 11, wherein the mycoherbicide composition further comprises an antibiotic.

* * * * *